United States Patent [19]

Fellman

[11] Patent Number: 5,232,914
[45] Date of Patent: Aug. 3, 1993

[54] SOLID, STORAGE-STABLE, GERMICIDAL, PRE-IODINE COMPOSITION

[75] Inventor: Jack H. Fellman, Portland, Oreg.

[73] Assignee: Epitope, Inc., Beaverton, Oreg.

[21] Appl. No.: 677,589

[22] Filed: Mar. 29, 1991

Related U.S. Application Data

[63] Continuation-in-part of Ser. No. 179,841, Apr. 11, 1988, abandoned.

[51] Int. Cl.$^5$ ............................................. A61K 33/18
[52] U.S. Cl. ..................................... 514/23; 514/728; 514/731; 424/667; 424/668; 424/669
[58] Field of Search ....................... 424/667, 668, 669; 514/718, 731, 24, 23

[56] References Cited

U.S. PATENT DOCUMENTS

| | | | |
|---|---|---|---|
| 1,661,640 | 3/1928 | Van Allen | 424/668 |
| 4,320,114 | 3/1982 | Denzinger et al. | 424/80 |
| 4,321,257 | 3/1982 | Sipos | 424/80 |

OTHER PUBLICATIONS

De Gruyter, Concise Encyclopedia of Biochemistry, 1983; Walter de Gruyter & Co. Berlin 30, pp. 505–506.

*Primary Examiner*—Ronald W. Griffin
*Assistant Examiner*—Pamela S. Webber
*Attorney, Agent, or Firm*—Eugene D. Farley

[57] ABSTRACT

A solid, storage-stable, germicidal, pre-iodine composition comprises in dry admixture with each other a solid oxy-compound of iodine, a solid reducing agent for the oxy-compound of iodine, and a solid desiccant used in amount sufficient to combine during the storage cycle of the composition with ambient and/or endogenous water. The oxy-compounds of iodine are iodic acid, iodine pentoxide, potassium iodate and sodium iodate. Preferred reducing agents are ascorbic acid, dihydroxy fumaric acid, the thiol sugars and cysteine. A preferred combination desiccant and iodine solvating agent is polyvinyl pyrrollidone having a molecular weight of from 10,000 to 1,000,000.

The composition is storage-stable for an indefinite period. Upon the addition of water, the oxy-compound of iodine is reduced to nascent iodine, which, in application, serves its well-known germicidal function.

16 Claims, No Drawings

[5,232,914]

SOLID, STORAGE-STABLE, GERMICIDAL, PRE-IODINE COMPOSITION

This application is a continuation-in-part of the U.S. patent application of Jack H. Fellman, Ser. No. 07/179,841 filed Apr. 11, 1988 for Solid, Storage-Stable, Germicidal, Pre-Iodine Composition, now abandoned.

This invention relates to storage-stable germicidal compositions of improved shelf life and containing iodine in precursor form.

Such compositions are termed herein "elemental-iodine-generating" germicidal compositions, or "pre-iodine" germicidal compositions. After storage, and upon the addition of water, the compositions have the capacity of immediately generating nascent iodine, useful as a germicide. In addition, they have the useful property of being compatible with supplemental germicidal agents such as the phenolic germicidal agents, and the quaternary ammonium salt germicides.

BACKGROUND AND GENERAL STATEMENT OF THE INVENTION

Although a wide variety of highly effective, aqueous, iodine-containing germicidal solutions are known and extensively used against a broad spectrum of microorganisms, their commercial application is attended by certain disadvantages inherent in the chemical nature of their principal component, iodine.

In the first place, since iodine is volatile, iodine-containing germicides in the form of either powders or solutions tend to lose iodine by sublimation and evaporation. Accordingly, the germicides are characterized by shelf lives of restricted duration.

In the second place, because of its extreme activity, the iodine tends to react with other ingredients of any aqueous germicidal composition in which it is contained, causing the composition to lose germicidal activity. By-products of such reactions, notably hydriodic acid, compound the problem because of their own per se chemical activity.

The general problem with the available aqueous iodine germicidal preparations is their instability, slowly but inexorably iodine in solution oxidizes the solvating co-ingredients such as ethanol in Tincture of Iodine, polyvinylpyrollidone in Betadine, and ethyleneoxides and alcohols in nonionic detergents such as Wescodine.

The iodide generated by these reactions ultimately forms the triiodide ion which will not penetrate microbial cell walls. It therefore is ineffective as a germicide.

Furthermore, iodine preparation such as those listed above cannot be co-mingled with other materials such as phenols and quaternary ammonium detergent germicides, or other chemically reactive substances. If so co-mingled, the undesirable degenerative reactions noted above occur and destroy the expected benefit of the co-mingling materials.

It has been proposed (Van Allen U.S. Pat. No. 1,661,640) to overcome the foregoing problem by preparing, storing and dispensing the iodophor in the form of a dry hygroscopic powder and then, just before the iodophor is to be applied, adding water to form the active germicidal solution.

The problem with this proposed routine is that the iodine compounds contained in the dry iodophor are extremely sensitive to the presence of water. The degradative reactions noted above are catalysed by the presence of only minute amounts of that substance.

In practice, the germicidal composition is exposed to water derived from two sources.

In the first place, it is impossible to exclude all traces of moisture from the containers in which the compositions are to be stored. This ambient moisture, even though present in minute amounts, suffices to initiate the reactions, by which the iodophor is converted to undesirable products.

In the second place, the reaction, once initiated, is auto-catalytic since it produces water as a product. This endogenous water further promotes the undesirable degradation reactions, which accordingly take place at an ever-increasing pace.

Nevertheless, in spite of these disadvantages, iodine is an extremely effective and widely used germicide. It has an impact on the entire spectrum of microorganisms including the human pathogens. Bacteria, both gram negative and gram positive; rickettsia, fungi, viruses and protozoan organisms all are effectively destroyed after exposure to dilute iodine solutions.

It accordingly would be desirable, particularly for military purposes, to provide in commercial form an iodine source, i.e. a light weight "pre-iodine", which is easily contained, stored and transported; which is stable and has infinite shelf life; which is compatible with selected supplemental germicides; but which, upon the addition of water, is converted instantly to a germicidal composition containing nascent Iodine and evidencing all of the desired germicidal qualities, making it useful in the usual applications to which iodine germicides are suited.

The foregoing and other objectives of my invention are achieved by the provision of a solid, storage-stable, germicidal, pre-iodine composition which, broadly stated, comprises a solid oxy-compound of iodine; a solid, water soluble, chemical reducing agent therefor; and a solid desiccant.

The oxy-compound of iodine furnishes the iodine content of the ultimate germicide. The reducing agent provides the means of unlocking the iodine from the oxy-compound of iodine when the composition is placed in water. The solid desiccant shields the other two components from the deleterious action of ambient or endogenous moisture to which they may inadvertently be exposed during the storage cycle.

In addition to the foregoing key ingredients, there may be incorporated in the composition suitable proportions of buffering agents to regulate the pH, solvating agents to increase the solubility of the components in water, and compatible co-germicides.

There thus is provided a pre-iodine composition which may be stored indefinitely in the solid form, but which upon the addition of water becomes instantly activated to generate a germicide containing elemental iodine and possessed in maximum degree of the desirable properties of germicides of this class.

DESCRIPTION OF PREFERRED EMBODIMENTS OF THE INVENTION

As noted, the composition of my invention comprises a solid, germicidal, pre-iodine composition designed for use in aqueous media but preliminary to such use storable dry in containers containing a small amount of ambient moisture without substantial degradative formation of triiodide ion. The principal components of the composition are:

solid oxy-compound of iodine a solid water soluble chemical reducing agent therefor a solid desiccant Oxy-compounds of iodine suitable for use in my germicidal pre-iodine compositions comprise those iodine compounds characterized by containing molecular oxygen and by being reactive with reducing agents to form elemental iodine. Illustrative of such compounds are:

iodic acid
iodine pentoxide
potassium iodate and sodium iodate

Oxy-compounds of iodine at other valence levels, such as hypoiodous acid and periodic acid and their salts conceivably might also be used. However, their application is academic in view of their scarcity and/or instability.

In some respects, iodine pentoxide is a preferred oxy-compound of iodine for use in the presently described compositions. Its determining properties are as follows:

It is available as a non-hygroscopic, dry solid.

It is stable over long periods of time. In particular, its iodine content does not volatilize, nor does it sublime.

It is stable even at elevated temperatures.

It is soluble in such solvents as ethyl alcohol, enabling effective application to the other constituents of the composition.

When salvated, it is easily reduced to free iodine by a variety of suitable reducing agents. It furnishes the two protons required for the reaction to proceed to the elemental iodine stage and accordingly acts as the iodinating agent of the composition.

As opposed to its salts, notably potassium iodate, when reduced to free iodine it does not produce any residual derivative salts which would affect adversely the solubility of co-ingredients of the composition by the "salting out" effect of such salts.

It is co-mixable with a wide variety of materials including buffering agents, reducing agents, solvating agents, and co-germicides which may be incorporated to advantage in the herein described germicidal compositions.

However, as will appear more fully hereinafter, the corresponding salts of iodic acid, namely potassium iodate and sodium iodate, under proper conditions also may be used to advantage.

With respect to the second key ingredient of the herein described pre-iodine germicidal compositions, the chemical reducing agent for the solid oxy-compound of iodine, a variety of reducing agents may be employed provided they meet two critical criteria.

First, the reducing agent must have an electromotive force (emf) sufficient to accomplish the desired result, i.e. the reduction of the oxy-compound of iodine to free iodine.

The second is that the reducing agent should be used in amount sufficient to reduce the iodine pentoxide to free iodine, but not substantially in excess of the stoichiometric amount required for that purpose. If such an excess were to be used, the reduction reaction would proceed past the free iodine stage to the stage at which iodine in ionic form would be produced, for example hydriodic acid.

Since the reduction of the oxy-compound of iodine requires an acidic medium, it is desirable that the reducing agent provide a source of protons and thus imparts the desired degree of acidity to the reaction mixture. A suitable degree of acidity is one in which the reaction mixture has a pH of from about pH 1 to about pH 7.

Suitable reducing agents for the present purpose are ascorbic acid
dihydro fumaric acid
thiol sugars such as dithio erythritol and dithio threitol
cysteine The reduction reaction may take two courses, depending upon the identify of the oxy-compound of iodine component. These are illustrated by the following equations:

Where the oxy-compound of iodine is iodine pentoxide the following equation is illustrative

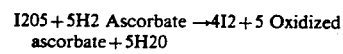
I2O5 + 5H2 Ascorbate → 4I2 + 5 Oxidized ascorbate + 5H2O

Where the oxy-compound of iodine is iodic acid, the illustrative equation is similar.

Where the oxy-compound of iodine is a salt of iodic acid, for example potassium iodate, the following equation is illustrative.

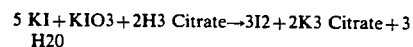
5 KI + KIO3 + 2H3 Citrate → 3I2 + 2K3 Citrate + 3 H2O

In the latter illustration, hydriodic acid generated by the action of citric acid on potassium iodide obviously is the active reducing agent. It has the apparent advantage of contributing to the active iodine content of the final germicidal composition. In addition, one of the protons provided by the citric acid is required to convert the potassium iodate to iodic acid.

In both illustrations, endogenous water is produced as an end product. The reaction accordingly is autocatalytic, since the presence of water is necessary for the reaction. The endogenous water thus produced drives the reaction to completion at an ever increasing tempo.

It therefore is important if the composition is to be container-stored in the dry state that the endogenous water, together with any ambient moisture present in the container, be removed as it is present and/or produced.

A further key component for the composition accordingly is an appropriate desiccant used in amount sufficient to tie up any ambient or endogenous moisture and thus render the composition storage stable for an infinite period.

The desiccant used thus must meet a unique problem. On the one hand, all traces of moisture, either ambient or endogenous, must be absent from the composition during its storage cycle. The presence of such moisture would auto-catalyze the reaction prematurely. On the other hand, the presence of water is necessary during the use cycle of the composition when it is desired to reduce the oxy-compound of iodine to elemental iodine.

A preferred desiccant for use in this difficult situation is polyvinyl pyrollidone having a molecular weight of from 10,000 to 1,000,000, preferably from 25,000 to 100,000.

However, other desiccants may be employed including the anhydrous inorganic salt desiccants such as anhydrous sodium sulphate, magnesium sulphate, and calcium chloride.

Other suitable drying agents include:
Polyvinyl alcohol
Polyethylene oxide derivatives of alcohols
Alkylethanolamines Nonionic detergents having melting points greater than 40 degrees C.

In addition to the oxy-compound of iodine, the reducing agent, and the desiccant, certain supplemental components may be included to impart desired properties to the germicidal pre-iodine compositions of my invention.

In particular, since iodine is soluble only with difficulty in aqueous media, a solvating agent may be used in amount sufficient to impart a desired degree of water solubility to the elemental iodine generated when, in use, water is added to the composition. A preferred solvating agent is polyvinylpyrollidone, described above in its application as a desiccant. It thus serves dual functions: that of a desiccant and that of a solvating agent for the iodine.

If it is desired to use the composition in the form of a dusting powder, from 0.01 to 99.09% by weight of starch or talc may be incorporated in the composition. A preferred dusting powder component is the starch product which has been first hydrolyzed and then modified by reaction with epichlorohydrin, i.e. the commercial product known as "modified dusting powder starch".

It also may be desirable to add to the composition one or more supplemental germicides, for example a quaternary ammonium salt such as undecoylium chloride, or environmental germicides such as ortho-phenyl phenol. As noted above, it is a particular feature of the invention that by its application reaction during storage of iodine with such co-germicides is prevented.

Still further, to control the pH of the final mixture to levels at which the mixture is stable and has an extended shelf life, it may be desirable to include a suitable buffering agent such as mono- or di-sodium phosphate used in amount sufficient to adjust the final pH to the desired level, i.e. to a level of from about pH 1 to about pH 7.

To insure long shelf life, the final mixture should be substantially dry. Its moisture content (not counting any water of hydration which may be present) should be controlled at a level of not over 5%, preferably not over 1%, by weight, dry solids basis.

The compositions of my invention are prepared simply by supplying the constituents in finely divided dry form and mixing them together intimately in suitable mixing equipment. They then may be stored indefinitely in a closed container.

After storage, to prepare a germicidal iodine solution, the dry powder is added to water in proportion predetermined to produce a solution of the desired concentration. The resulting iodine-containing solution then is employed in its germicidal applications in the usual manner.

If the compositions are provided in the form of dusting powders, the powders may be dusted on the inside of natural or synthetic rubber gloves and the gloves placed on the hands. Thereupon the perspiration generated will be sufficient to supply the moisture needed for conversion of the oxy-iodine content to elemental iodine.

A typical composition of the invention is set forth in the table below:

| Iodine Pentoxide | 1 equivalent |
| Reducing Agent | 0.8 to 1.2 equivalents |
| Iodine solvating agent and desiccant | Iodine solvating and desiccant quantity |

The invention is further illustrated by the following examples

|  | Example 1 | Example 2 | Example 3 |
| --- | --- | --- | --- |
| Iodine Pentoxide | 0.065 gm | 0.132 gm | 0.195 gm |
| Ascorbic Acid | 0.172 gm | 0.343 gm | 0.516 gm |
| Polyvinyl pyrollidone | 0.5 gm | 0.75 gm | 1.0 gm |
| Final Iodine Concentration | 0.5% | 1.0% | 1.5% |
| In use, add water to 10 ml final volume | | | |

The following example illustrates the use of a salt of iodic acid as the oxy-compound of iodine.

| Potassium iodide | 0.830 grams |
| Potassium iodate | 0.214 grams |
| Anhydrous citric acid | 0.192 grams |
| Dry polyvinyl pyrrollidine (35,000–50,000 molecular weight) | 0.4 grams |

The following example illustrates the importance of including an appropriate quantity of a suitable desiccant during the storage cycle of the herein described germicidal composition.

As fully developed above, the compositions are designed to be stored indefinitely in bottles or suitable containers which also contain a certain amount of residual air. Although the compositions are thoroughly dried before introduction into the containers, there necessarily is a minute amount of moisture contained in the residual air content of the containers. This small amount of moisture suffices to initiate during storage the reduction of the oxy-compound of iodine. This reaction produces water as a reaction product. The reaction thus is auto-catalytic and proceeds at an ever increasing rate until the composition is rendered useless as a germicide.

In the following experiments, the storage conditions of the germicidal composition are simulated, with and without the presence of a desiccant.

Each of 5 bottles, volume 250 ml, was fitted with a screw top cap penetrated by a wire to which a 1 cm. filter paper was appended.

Each bottle was charged with 1.24 gms. of a mixture containing 0.830 g KI, 0.214 g KIO3, and 0.192 g anhydrous citric acid. These components previously had been dried in a vacuum oven at 85 degrees C.

To each wick was added sufficient water to provide a final percentage of 0, 1%, 2%, 3%, 5%, 7% water in the bottle. The bottles were allowed to come to an equilibrium and the free iodine determined.

A similar experiment was constructed in which 1.2 gms of a mixture of 0.334 gms of I2O5 and 0.880 gms, of ascorbic acid were employed in place of the KI, KIO3, and citric acid employed in the first experiment.

Observation of the bottles in the first experiment revealed that within ten minutes all the contents of the bottles had reacted to completion.

In the second experiment the same end result was obtained although the rate of reaction was slower. It required 3 days for completion.

Both series of experiments were repeated, but with the addition of 12 grams of polyvinyl pyrollidone (PVP) to each of the bottles. In all cases, up to and including the experiment in which 5% water was added, the compositions remained indefinitely stable.

Exposure to water in amount greater than 10% resulted in slow but unacceptable iodine formation.

Having thus described in detail preferred embodiments of the present invention, it will be apparent to those skilled in the art that various changes may be made in the compositions described herein without altering the inventive concepts and principles embodied. The present embodiments are therefore to be considered in all respects as illustrative and not restrictive, the scope of the invention being indicated by the appended claims.

I claim:

1. A solid, storage-stable, elemental-iodine-generating (pre-iodine), germicidal composition designed for use in aqueous media but preliminary to such use storable in environments containing ambient moisture the composition comprising:
   a) a solid oxy-compound of iodine,
   b) a solid, water soluble, chemical reducing agent therefor having a degree of acidity and an electromotive force sufficient to reduce the oxy-compound of iodine to elemental iodine when in contact with the oxy-compound of iodine in an aqueous medium, the reducing agent being used in amount up to about the stoichiometric amount whereby to reduce the oxy-compound of iodine substantially to elemental iodine but without substantial formation of triiodide ion and with the concomitant production of endogenous water of reaction, and
   c) at least one solid desiccant selected from the group consisting of
      inorganic salt desiccants, polyvinyl alcohol desiccants, polyethylene oxide derivatives of alcohols desiccants, alkylethanolamine desiccants, and nonionic detergent desiccants having melting points greater than 40 degrees C.
   used in amount sufficient to combine during the storage cycle of the composition with said ambient moisture and with said endogenous water in substantially the amounts in which they are present and/or produced, thereby preserving the solid composition for subsequent introduction into an aqueous medium preliminarily to its intended germicidal application.

2. The pre-iodine composition of claim 1 wherein the desiccant is polyvinyl pyrollidone.

3. The pre-iodine composition of claim 2 wherein the desiccant is polyvinyl pyrollidone having a molecular weight of from 10,000 to 1,000,000.

4. The pre-iodine composition of claim 1 wherein the desiccant is an anhydrous inorganic salt desiccant.

5. The pre-iodine composition of claim 1 wherein the oxy-compound of iodine is at least one member of the group consisting of iodine pentoxide, iodic acid, potassium iodate and sodium iodate.

6. The pre-iodine composition of claim 1 wherein the reducing agent is at least one member of the group consisting of ascorbic acid, dihydroxy fumaric acid, the thiol sugars and cysteine.

7. The pre-iodine composition of claim 1 wherein the oxy-compound of iodine is at least one member of the group consisting of iodine pentoxide, iodic acid, potassium iodate and sodium iodate and wherein the reducing agent is at least one member of the group consisting of ascorbic acid, dihidroxy fumaric acid, the thiol sugars and cysteine.

8. The pre-iodine composition of claim 7 wherein the oxy-compound of iodine is iodine pentoxide and the reducing agent is ascorbic acid.

9. The pre-iodine composition of claim 1 wherein the oxy-compound of iodine is an alkali metal iodate and the reducing agent is an alkali metal iodide used together with a pH control agent used in amount sufficient to impart a pH of from about 1 to about 7 to the composition when dissolved in water.

10. The pre-iodine composition of claim 1 wherein the oxy-compound is potassium iodate and the reducing agent is a mixture of potassium iodide, ascorbic acid and pH control agent.

11. The pre-iodine composition of claim 1 wherein the moisture content of the composition is not over about 5% by weight of the composition, dry solids basis.

12. The pre-iodine composition of claim 1 including a germicidal proportion of ortho-phenyl phenol.

13. The pre-iodine composition of claim 1 including a germicidal proportion of a germicidal quaternary ammonium salt.

14. The pre-iodine composition of claim 1 for use as a dusting powder in surgical gloves and like applications and including from 0.01 to 99.99 parts by weight of starch or talc as a solid filler material.

15. The pre-iodine composition of claim 8 wherein the oxy-compound of iodine is iodine pentoxide used in the amount of one part by weight and the reducing agent is ascorbic acid used in the amount of from 2.5 to 2.7 parts by weight.

16. The pre-iodine composition of claim 1 wherein the oxy-compound of iodine is about 1 equivalent of potassium or sodium iodate and the reducing agent is a mixture of about 5 equivalents of sodium or potassium iodide, about 2 equivalents of citric acid, and a pH control agent used in amount sufficient to adjust the pH of the final composition when dissolved in water to a value of from about pH 1 to about pH 7.

* * * * *